United States Patent
Fukutomi et al.

(10) Patent No.: US 7,601,201 B2
(45) Date of Patent: Oct. 13, 2009

(54) METHOD OF REMOVING CARBON MONOXIDE FROM AN OXYGEN CARRIER AND APPARATUS FOR REMOVING CARBON MONOXIDE

(75) Inventors: Ippei Fukutomi, Osaka (JP); Toshiya Kai, Osaka (JP); Naohisa Katayama, Osaka (JP); Takeshi Nizuka, Osaka (JP); Yoshinori Kida, Osaka (JP)

(73) Assignee: Nipro Corporation, Osaka (JP)

( * ) Notice: Subject to any disclaimer, the term of this patent is extended or adjusted under 35 U.S.C. 154(b) by 507 days.

(21) Appl. No.: 11/403,188

(22) Filed: Apr. 13, 2006

(65) Prior Publication Data

US 2006/0249456 A1    Nov. 9, 2006

(30) Foreign Application Priority Data

Apr. 15, 2005 (JP) ............................. 2005-119057
Feb. 16, 2006 (JP) ............................. 2006-038716

(51) Int. Cl.
  *B01D 53/22* (2006.01)
  *C07K 14/80* (2006.01)
  *C02F 1/44* (2006.01)

(52) U.S. Cl. ................ 95/46; 95/51; 95/54; 95/230; 96/6; 96/8; 96/10; 96/230; 210/640; 210/641; 210/748; 210/500.23; 604/5.01; 604/6.08; 423/246; 423/247; 422/186.3; 514/6; 530/385; 424/530

(58) Field of Classification Search ........... 95/46, 95/51, 54, 230; 96/6, 8, 10, 243; 210/640, 210/641, 748, 500.23; 604/5.01, 6.08; 423/219, 423/246, 247, 579; 422/186.3; 514/6, 21; 530/302, 363, 385; 424/529, 530

See application file for complete search history.

(56) References Cited

U.S. PATENT DOCUMENTS

| | | | | |
|---|---|---|---|---|
| 4,343,715 A | * | 8/1982 | Bonaventura et al. | 95/230 |
| 4,542,010 A | * | 9/1985 | Roman et al. | 423/579 |
| 4,609,383 A | * | 9/1986 | Bonaventura et al. | 95/46 |
| 5,773,417 A | * | 6/1998 | Bonaventura | 514/21 |
| 5,862,449 A | * | 1/1999 | Bischoff et al. | 422/186.3 |
| 2002/0095108 A1 | * | 7/2002 | Tsuchida et al. | 604/6.08 |
| 2005/0016907 A1 | * | 1/2005 | Yuen | 422/186.3 |
| 2005/0040029 A1 | * | 2/2005 | Monzyk et al. | 422/186.3 |

FOREIGN PATENT DOCUMENTS

| | | |
|---|---|---|
| EP | 1 093 720 A1 | 4/2001 |
| JP | 10-263535 | 10/1998 |
| JP | 11-023545 | 1/1999 |
| JP | 2001-232380 | 8/2001 |
| WO | 96/03426 A1 | 2/1996 |

OTHER PUBLICATIONS

Kluger, Ronald et al., "Chemical Cross-Linking and Protein-Protein Interactions-A Review With Illustrative Protocols", *Bioorganic Chemistry*, vol. 32 No. 6 (2004) pp. 451-472.

* cited by examiner

*Primary Examiner*—Jason M Greene
(74) *Attorney, Agent, or Firm*—Kubovcik & Kubovcik

(57) ABSTRACT

A method of removing carbon monoxide from an oxygen carrier including setting a carbon monoxide bonded oxygen carrier solution across a separation membrane from an oxygen-dissolved solution; and exposing the setting part to the light and a method of removing carbon monoxide from an oxygen carrier including setting a carbon monoxide oxygen carrier solution across a hollow fiber separation membrane from an oxygen-dissolved solution; and exposing the setting part to light.

6 Claims, 11 Drawing Sheets

Prior Art

METHOD OF REMOVING CARBON MONOXIDE FROM AN OXYGEN CARRIER AND APPARATUS FOR REMOVING CARBON MONOXIDE

TECHNICAL FIELD

The present invention relates to a method of treating an oxygen carrier. The present invention more specifically relates to a method of treating an aqueous solution containing a carbon monoxide bonded oxygen carrier, that is, a method of performing a carbon monoxide removal treatment on an oxygen carrier to remove carbon monoxide for the stabilization of the oxygen carrier. Carbon monoxylation of an oxygen carrier is used for preventing inactivation of an oxygen transport function of hemoglobin over a long period of time. The present invention also relates to an oxygen carrier subjected to the treatment, and to an apparatus for the treatment.

PRIOR ART

As oxygen carriers, there are natural oxygen carriers and artificial oxygen carriers. Examples of the natural oxygen carriers include hemoglobin originated from, for example, humans, bovines, or other living organisms; concentrated red blood cells or myoglobin originated from, for example, humans, bovines, or other living organisms; and hemocyanin originated from, for example, fish or other living organisms. Examples of the artificial oxygen carriers include highly-functional oxygen carriers that utilize natural oxygen carriers, such as modified hemoglobin and hemoglobin-encapsulated liposomes; completely-synthesized oxygen carriers, such as compounds in which porphyrin metallic complexes inclusive of porphyrin derivatives are incorporated in albumin, albumin dimers, and albumin polymers; and perfluorocarbons; and recombinant oxygen carriers, such as recombinant hemoglobin, recombinant modified hemoglobin, modified recombinant hemoglobin, and recombinant hemoglobin-encapsulated liposomes, which can be obtained by gene recombination technologies. These oxygen carriers can replace red blood cells of humans and other animals.

These oxygen carriers are used for oxygen supply to an ischemic site or tumor tissue, for blood transfusion to a patient with massive bleeding, for an organ-preserving perfusion fluid, for an extracorporeal circulation fluid, for a cell culture medium, and so on (see, e.g., Patent Document 1 or 2 or Non-Patent Document 1 identified below).

An example of the porphyrin metal complex is a 2-[8-(2-methyl-1-imidazolyl)octanoyloxymethyl]-5,10,15,20-tetrakis[$\alpha,\alpha,\alpha,\alpha$-o-(1-methylcyclohexanoylamino)phenyl]porphinato complex (Non-patent Document 2 identified below).

The hemoglobin-encapsulated liposome includes a hemoglobin encapsulated in an inner layer of a liposome formed of a lipid bilayer, and various preparation methods and investigations thereof have been studied (Patent Document 1 identified below).

The artificial oxygen carriers having divalent heme iron in an artificial oxygen carrier molecule have an oxygen transport function. An artificial oxygen carrier having the heme iron oxidized into trivalent heme iron, that is, an artificial oxygen carrier which loses an ability of oxygen coordination has no oxygen transport function. Thus, formation of the artificial oxygen carrier which loses the ability of oxygen coordination must be prevented. A known method of preventing the formation of the artificial oxygen carrier which loses the ability of oxygen coordination involves formation of a complex of heme iron and carbon monoxide in the artificial oxygen carrier molecule, that is, stabilization of the artificial oxygen carrier through carbon monoxylation (Non-patent Document 3, for example, identified below).

The artificial oxygen carrier which is stabilized through formation of a complex of heme iron bonded carbon monoxide (hereinafter sometimes referred to as a carbon monoxide bonded artificial oxygen carrier) has no oxygen transport function. Thus, carbon monoxide which forms the complex with heme iron in the artificial oxygen carrier must be removed, in other words, de-carbon monoxylation must be carried out, before the carbon monoxide bonded artificial oxygen carrier is used as a red blood cell alternative, for recovering the oxygen transport function of the artificial oxygen carrier.

A known method of recovering the oxygen transport function by removing carbon monoxide from the carbon monoxide bonded artificial oxygen carrier involves introducing an artificial oxygen carrier solution into a round bottom flask in a volume of about $\frac{1}{100}$ of that of the flask; exposing the solution in an ice bath to light of 200 W; and blowing oxygen into the solution for 10 minutes while the flask is rotated (Non-patent Document 4, for example, identified below).

A known modified method thereof involves using a hollow fiber formed of a porous hollow fiber membrane; applying an oxygen gas pressure through the hollow fiber membrane from the outer side of the membrane; allowing passage of an aqueous solution containing a carbon monoxide bonded artificial oxygen carrier from an inner side of the hollow fiber membrane; and removing carbon monoxide from the artificial oxygen carrier in the aqueous solution under light (Patent Document 3, for example, identified below).

Patent Document 1: JP 2004-307404 A, paragraph [0008], paragraph [0009], or Examples in paragraph [0039] regarding a method of preparing a hemoglobin-encapsulated liposome.

Patent Document 2: JP 2004-277329 A paragraph [0002] or paragraph [0003].

Patent Document 3: JP 06-329550 A, paragraph [0008] and the like.

Non-patent Document 1: Komatsu et al., Artificial blood, vol. 6, pp. 110-114, 1998, lines 16 to 19, left hand column, p. 111.

Non-patent Document 2: Bioconjugate Chem., vol. 13, p. 397-402, 2002.

Non-patent Document 3: Methods in ENZYMOLOGY, vol. 76, HEMOGLOBINS, ACADEMIC PRESS, p. 9, 1981.

Non-patent Document 4: Methods in ENZYMOLOGY, vol. 76, HEMOGLOBINS, ACADEMIC PRESS, p. 164, 1981.

DISCLOSURE OF THE INVENTION

Problems to be Solved by the Invention

The conventional methods of recovering an oxygen transport function of a carbon monoxide bonded oxygen carrier have low productivity because treatment in a round bottom flask, for example, is a batch method involving introducing the carbon monoxide bonded oxygen carrier and recovering the oxygen carrier each time.

Both in the treatment in a round bottom flask and in a modified method using a hollow fiber, oxygen is supplied as a gas. Thus, the artificial oxygen carrier concentrates by solvent scattering from the artificial oxygen carrier, to thereby cause denaturation of proteins and the like. At the same time, a surface of a hollow fiber membrane become dry by solvent vaporization, to thereby degrade permeability of the hollow fiber membrane and the other properties.

Further, an oxygen gas has a low heat exchange rate, and heat accumulation is easily caused by light. As a result, degradation of a hollow fiber membrane and denaturation of the artificial oxygen carrier are liable to occur.

Means for Solving the Problem

The present invention has been made in view of the above-mentioned problems. The inventors of the present invention have conducted extensive studies, and have found that an oxygen carrier subjected to carbon monoxide removal can be obtained by sandwiching a separation membran between a carbon monoxide bonded oxygen carrier solution and a solution in which oxygen is dissolved (hereinafter referred to as an oxygen-dissolved solution); and exposing the separation membrane as a reaction plane to light, i.e., a plane where light raises electrons from one energy level to another and carbon monoxide comes free the oxygen carrier and the oxygen carrier without a ligand coordinates oxygen. Thus, the inventors have completed the present invention.

That is, the present invention relates to the following.

(1) A method of removing carbon monoxide from a carbon monoxide bonded oxygen carrier comprising:
setting a carbon monoxide bonded oxygen carrier solution across a separation membrane from an oxygen-dissolved solution; and exposing the separation membrane as a reaction plane to light.

(2) The method of removing carbon monoxide from a carbon monoxide bonded oxygen carrier according to the above item (1), in which the separation membrane is a hollow fiber separation membrane.

(3) An oxygen carrier, which is obtained such that a carbon monoxide bonded oxygen carrier solution is set across a separation membrane from an oxygen-dissolved solution, and carbon monoxide is removed from the carbon monoxide bonded oxygen carrier by exposing the separation membrane as a reaction plane to light.

(4) The oxygen carrier according to the above item (3), which is one material or a combination of two or more kinds selected from the group consisting of a hemoglobin-encapsulated liposome; a porphyrin metal complex-including albumin; a porphyrin metal complex/PEGylated albumin composite; a hemoglobin solution; a cross linked hemoglobin; a polymerized hemoglobin; and a PEGylated hemoglobin.

(5) A pharmaceutical composition including: one or two or more kinds of agents selected from the group consisting of a reducing agent, electrolytes, saccharides, a pH adjuster, an isotonizing agent, and a polymer substance capable of imparting a colloid osmotic pressure; and the carbon monoxide bonded oxygen carrier according to the above item (3).

(6) A separation membrane for removing carbon monoxide from an oxygen carrier, across which the carbon monoxide bonded oxygen carrier solution is set apart from an oxygen-dissolved solution; and exposing the separation membrane as the reaction plane to light.

(7) A separation membrane module, containing the separation membrane for removing carbon monoxide according to the above item (6).

(8) The separation membrane module according to the above item (7), in which a separation membrane is placed only in a portion to be exposed as the reaction plane to light.

(9) An apparatus for removing carbon monoxide from an carbon monoxide bonded oxygen carrier comprising:

a separation membrane for separating a carbon monoxide bonded oxygen carrier solution (across the separation membrane) from an oxygen-dissolved solution;
a light source for exposing the separation membrane as a reaction plane to light; and
pumps for supplying respective solutions.

Effects of the Invention

The method of removing carbon monoxide from an oxygen carrier according to the present invention including setting a carbon monoxide bonded oxygen carrier solution across a separation membrane from an oxygen-dissolved solution, and exposing the separation membrane as a reaction plane to light, can prevent denaturation of proteins and the like by concentration of the oxygen carrier. At the same time, the method can prevent degradation of membrane performance related to drying of the separation membrane.

Further, a large heat exchange rate between solutions can suppress heat accumulation by light, to thereby prevent degradation of the separation membrane and denaturation of the oxygen carrier by heat.

An apparatus system for performing continuous treatment of removing carbon monoxide from an oxygen carrier can be designed by using the separation membrane. Thus, productivity can be enhanced compared with that of a batch method such as conventional treatment in a round bottom flask.

Furthermore, the oxygen carrier passes only through a light exposing portion when the separation membrane is placed only in a surface or so portion of a membrane module to be exposed as the reaction plane to light. Thus, removal of carbon monoxide can be more effectively carried out.

Figure 1:
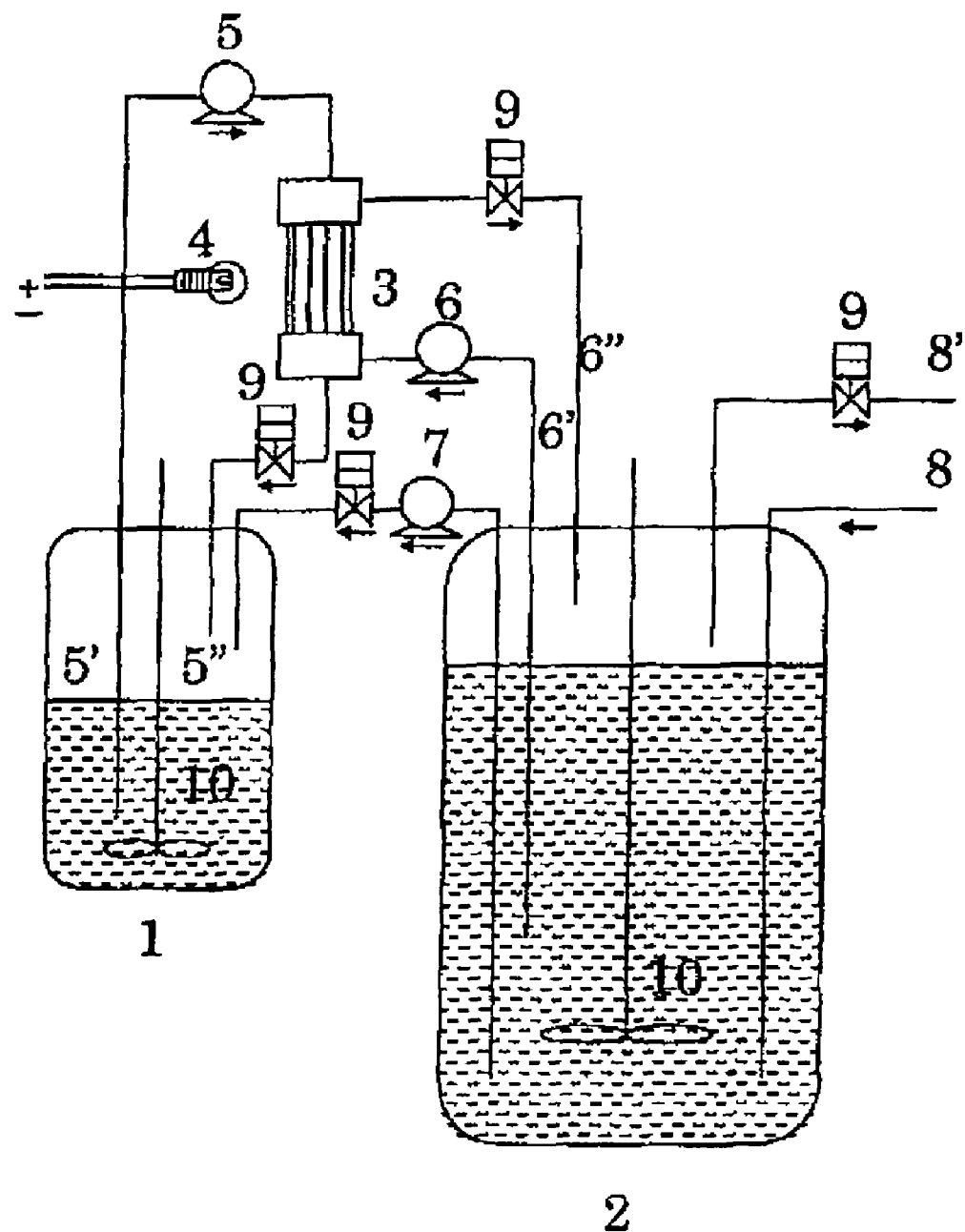
FIG. 1 shows a diagram explaining an apparatus for removing carbon monoxide according to the present invention with a hollow fiber membrane by using an oxygen-dissolved solution. Vertical lines of the hollow fiber module 3 represent the vertical arrangement of hollow fibers.

DESCRIPTION OF SYMBOLS 1 oxygen carrier circulation vessel
2 oxygen-dissolved solution circulation vessel
3 hollow fiber membrane module
3' planar membrane module
4 light source
5 oxygen carrier circulation pump
5' oxygen carrier supply line
5" oxygen carrier recovery line
6 oxygen-dissolved solution circulation pump
6' oxygen-dissolved solution supply line
6" oxygen-dissolved solution recovery line
7 oxygen-dissolved solution supply pump
8 oxygen supply line
8' gas discharge line
9 flow control valve
10 stirrer and blade thereof
11 oxygen carrier circulation vessel
12 oxygen gas supply line
12' gas discharge line
13 hollow fiber membrane module
14 light source oxygen carrier circulation pump
16 oxygen gas supply pump
17 oxygen carrier storage vessel
18 oxygen-dissolved solution circulation vessel
19 hollow fiber membrane module A
20 hollow fiber membrane module B
21 hollow fiber membrane module C
22 light source A
23 light source B
24 light source C
25 oxygen carrier circulation pump
25' oxygen carrier supply line
25" oxygen carrier recovery line
26 oxygen-dissolved solution circulation pump
26' oxygen-dissolved solution supply line
26" oxygen-dissolved solution recovery line
27 oxygen supply line
27' gas discharge line
28 vessel for recovering an oxygen carrier subjected to carbon monoxide removal
29 oxygen carrier storage vessel
30 oxygen-dissolved solution circulation vessel
31 urethane-sealed hollow fiber membrane module
32 light source A
33 oxygen carrier circulation pump
33' oxygen carrier supply line
33" oxygen carrier recovery line
34 oxygen-dissolved solution circulation pump
34' oxygen-dissolved solution supply line
34" oxygen-dissolved solution recovery line
35 oxygen supply line
35' gas discharge line
36 vessel for recovering an oxygen carrier subjected
37 flow path direction of an oxygen-dissolved solution within the hollow fiber membrane.
38 flow path direction of an oxygen carrier solution in the outside of the hollow fiber membrane.

BEST MODE FOR CARRYING OUT THE INVENTION

The present invention relates to a method of removing carbon monoxide from an oxygen carrier including setting a carbon monoxide bonded oxygen carrier solution across a separation membrane from an oxygen-dissolved solution, and exposing the portion of the membrane separating the solutions, i.e., the setting part, to light; to an oxygen carrier subjected to carbon monoxide removal, and to an apparatus for removing carbon monoxide.

An apparatus such as that shown in FIG. 1, in which a carbon monoxide bonded oxygen carrier solution circulates, may be used for performing the method of the present invention. That is, the apparatus includes an oxygen carrier circulation vessel 1; an oxygen-dissolved solution circulation vessel 2; a hollow fiber membrane module 3; a light source 4; an oxygen carrier circulation pump 5; an oxygen-dissolved solution circulation pump 6; an oxygen-dissolved solution supply pump 7; an oxygen supply line 8; and a flow control valve 9.

In the apparatus shown in FIG. 1, an oxygen carrier supplied from the oxygen carrier circulation vessel 1 with pump 5 is subjected to carbon monoxide removal by an oxygen-dissolved solution supplied from the oxygen-dissolved solution circulation vessel 2 and light from the light source 4 in the hollow fiber membrane module 3, and then is returned to the oxygen carrier circulation vessel 1.

Meanwhile, oxygen-dissolved solution supplied from the oxygen-dissolved solution circulation vessel 2 with pump 6 supplies oxygen into the hollow fiber membrane module 3 and receives carbon monoxide from the oxygen carrier, and then is returned to the oxygen-dissolved solution circulation vessel 2. Carbon monoxide in the returned solution is discharged from the returned solution through a gas discharge line 8', as the returned solution is replenished with oxygen gas from the oxygen supply line 8.

Figure 4:
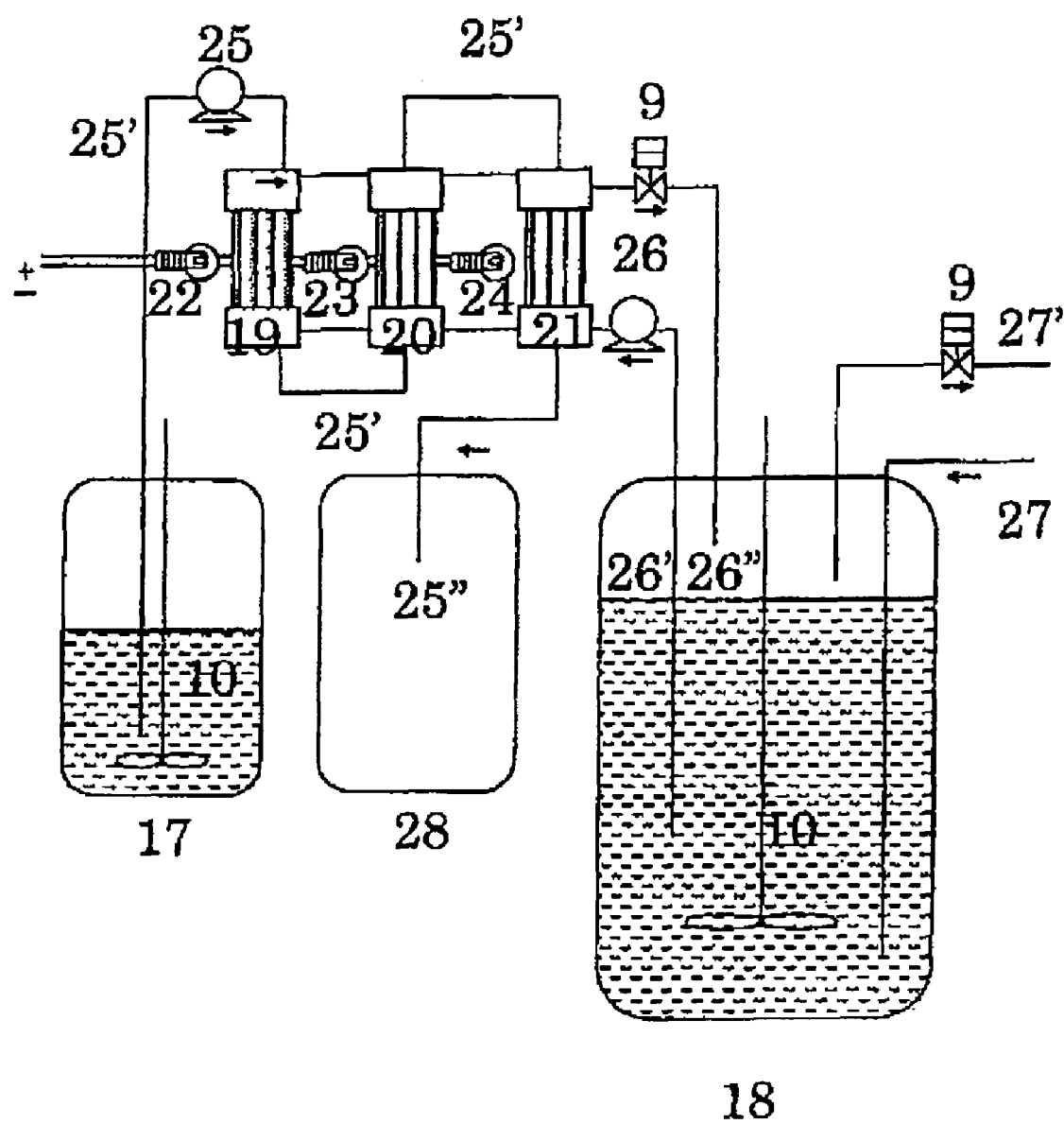
FIG. 4 shows a diagram explaining an apparatus for continuously removing carbon monoxide according to the present invention with a hollow fiber membrane by using an oxygen-dissolved solution. Vertical lines of the hollow fiber modules 19, 20, 21 represent the vertical arrangement of hollow fibers.

Further, an apparatus such as that shown in FIG. 4, in which an oxygen carrier is recovered continuously without circulation of a carbon monoxide bonded oxygen carrier solution, may be used for performing the method of the present invention. That is, the apparatus includes: an oxygen carrier storage vessel 17; an oxygen-dissolved solution circulation vessel 18; a hollow fiber membrane module A 19; a hollow fiber membrane module B 20; a hollow fiber membrane module C 21; a light source A 22; a light source B 23; a light source C 24; an oxygen carrier circulation pump 25; an oxygen-dissolved solution circulation pump 26; an oxygen supply line 27; and a vessel 28 for recovering an oxygen carrier subjected to carbon monoxide removal. In this apparatus, the oxygen carrier subjected to carbon monoxide removal can be recovered continuously, to thereby drastically enhance its production efficiency.

As described above, apparatus of the present invention are shown in FIGS. 1 and 4, for example, but the present invention is obviously not limited thereto.

The oxygen carrier to be used in the present invention with divalent heme iron in an oxygen carrier molecule has an oxygen transport function. The oxygen carrier may be one material or a combination of two or more kinds of materials selected from, for example, the group consisting of a hemoglobin-encapsulated liposome; a porphyrin metal complex-including albumin, a porphyrin metal complex/PEGylated albumin composite, a hemoglobin solution, a molecular bridge-hemoglobin, a hemoglobin polymer, and a PEG-hemoglobin polymer.

The oxygen carrier to be used may have a particle size of about 5 nm to 8 μm, and preferably about 5 nm to 450 nm to be used as a red blood cell alternative.

In the method of removing carbon monoxide from an oxygen carrier according to the present invention, a separation membrane to be used may be in a planar form or a hollow fiber form. A material for the separation membrane is generally a material used for an ultrafiltration membrane or a filtration filter, and is preferably polysulfone, cellulose triacetate, cellulose diacetate, polycarbonate, polyethersulfone, or a polyphospholipid polymer.

The size of pores present on the surface of the membrane may be selected in accordance with the particle size of the oxygen carrier, and the pore size must be smaller than the particle size of the oxygen carrier. The separation membrane to be used has a pore size of generally 5,000 nm to 0.001 nm, and preferably 10 nm to 0.10 nm. The form of the separation membrane is not particularly limited. A planar separation membrane is advantageous in view of light exposure, but a hollow fiber separation membrane may also be used.

The separation membrane module as used in the present invention refers to a unit for protecting a separation membrane and retaining the separative power thereof, which is constructed of, for example, a separation membrane for removing carbon monoxide, a housing for fixing and protecting the separation membrane, a connector for securing a flow path, and a gasket for isolation of a flow path and prevention of liquid leakage. When a hollow fiber is used as a separation membrane, it is referred to as a hollow fiber membrane module. In contrast, when a planar membrane is used, it is referred to as a planar membrane module. The separation membrane module can be provided in planar form or in cylindrical form described later when the hollow fiber membrane module is configured as the setting part of hollow fibers.

The case so called housing of the separation membrane module is preferably made of an optically transparent material and at least part of the case, in which the planar membrane or hollow fiber membrane is arranged, is preferably transparent or translucent to transmit light.

In general, the hollow fiber membrane modules in which hollow fibers are arranged in cylindrical cases are popularly used. In the present invention, for example, hollow fiber membrane modules FB-50UGA (manufactured by NIPRO Corporation) and FB-210UGA (manufactured by NIPRO Corporation) can be used. Furthermore, the arrangement of the setting part (as defined below) of the separation membrane only on the light exposing portion leads to an increased opportunity for contact between a carbon monoxide bonded oxygen carrier solution and an oxygen-dissolved solution, and also leads to an increased reaching degree of light, i.e., an increased ratio of oxygen carrier exposed to light, thereby enhancing the efficiency of removing carbon monoxide from the oxygen carrier in the separation membrane module.

The setting part of the separation membrane only on the light exposing portion means that the separation membrane is placed such that the separation membrane can be sufficiently exposed to light. Such a setting part of the separation membrane may be, for example, one in which the separation membrane is placed to diminish a dead space between the separation membrane and the case; or one in which the central part of the separation membrane module, where light hardly reaches, is reduced in size as much as possible.

For instance, in the above hollow fiber membrane module in cylindrical form, the central portion of a main body case may be filled with a filler to prevent the passage of a sample solution therethrough (FIG. 9) to allow the effective hollow fiber membrane to be stacked in a thickness of 1 cm or less from the lateral side of the case cylinder so as to be placed on the inner surface of the cylindrical case (housing). Thus, it is preferable because of an effective removal of carbon monoxide due to the passage of the oxygen carrier solution, which requires the removal of carbon monoxide, only through the light exposed portion on the surface without passing through the central portion of the hollow fiber membrane module.

In this case, for example, the hollow fiber membrane module may be of an improved version in which a hollow fiber membrane is previously placed on the inner surface of the main body case, an improved version in which the central portion of a normal dialyzer is sealed with a water-impermeable resin, such as urethane, to allow the passage only through the surface of the cylinder, or an improved version in which hollow fibers are placed in a flat case such that the hollow fibers will be in the form of a planar layer of 1 cm or less in thickness.

Figure 3:
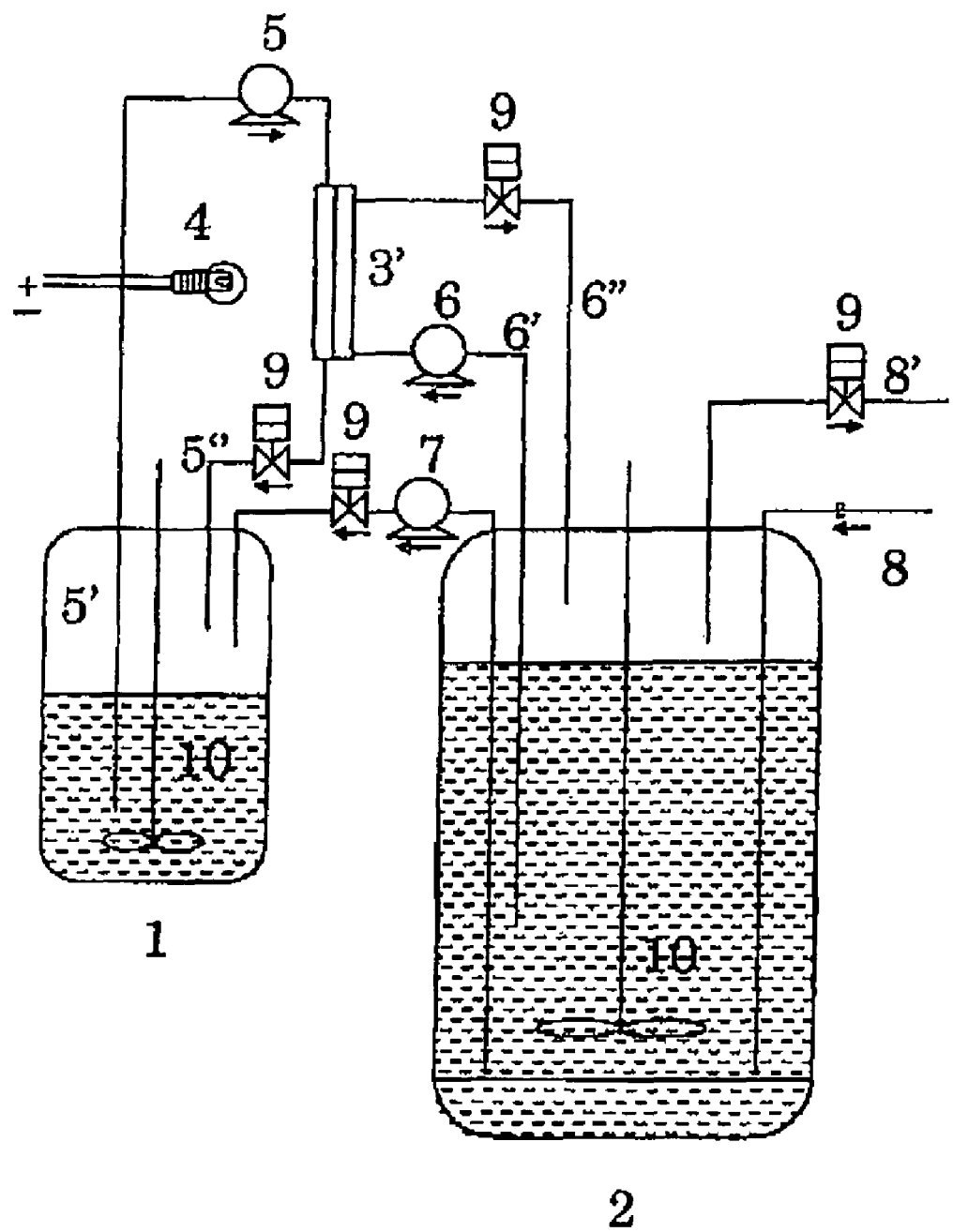
FIG. 3 shows a diagram explaining an apparatus for removing carbon monoxide according to the present invention with a planar membrane by using an oxygen-dissolved solution. A planar membrane module 3' represents its configuration shown from the side surface and is formed of a planar membrane having a depth in fact. The vertical lines show the planar hollow fiber membranes of the end portions in the square type membrane module 3'.

An apparatus employing a separation membrane in a planar form may be an apparatus as shown in FIG. 3, for example. That is, the apparatus includes an oxygen carrier circulation vessel 1; an oxygen-dissolved solution circulation vessel 2; a planar membrane module 3'; a light source 4; an oxygen carrier circulation pump 5; an oxygen-dissolved solution circulation pump 6, an oxygen-dissolved solution supply pump 7; and an oxygen supply line 8. This apparatus allows uniform light exposure from the light source and is efficient.

The setting of a carbon monoxide bonded oxygen carrier solution across a separation membrane from an oxygen-dissolved solution according to the present invention refers to setting in which the carbon monoxide bonded oxygen carrier solution is provided on one side of the separation membrane as a boundary and the oxygen-dissolved solution is provided on another side thereof. With this apparatus, the separation membrane has a function of allowing free passage of a solvent, ions, dissolved oxygen in the oxygen-dissolved solution, or carbon monoxide without separation, preventing passage of the oxygen carrier for its separation. Thus, the carbon monoxide bonded oxygen carrier is subjected to carbon monoxide removal by means of oxygen and light supplied through the separation membrane while the carbon monoxide bonded oxygen carrier maintains its concentration.

The carbon monoxide bonded oxygen carrier solution may be circulated or the oxygen carrier solution subjected to carbon monoxide removal may be collected without being circulated. Collecting without being circulated enables continuous production of the oxygen carrier solution subjected to carbon monoxide removal. A supply speed of the carbon monoxide bonded oxygen carrier solution may be determined arbitrarily in accordance with the performance of the separation membrane and the like, and a supply amount of the carbon monoxide bonded oxygen carrier solution per unit area of the membrane is preferably 1 L/min/m$^2$ or less.

The oxygen-dissolved solution means a solution containing oxygen dissolved therein by bubbling a pure oxygen gas, air, or the like or by applying pressure to the solution. An oxygen concentration in the solution is not particularly limited, and the solution may be saturated. The oxygen-dissolved solution may be circulated or disposed after use, but is more economically circulated. Oxygen to be supplied also serves to discharge and remove, as a gas, carbon monoxide in the solution circulated and returned from the separation membrane. The dissolved oxygen concentration is preferably 4 ppm or more.

The circulation rate of the oxygen-dissolved solution is affected by properties of the separation membrane. The circulation rate must be set such that a pressure of the oxygen carrier solution to be circulated in a normal direction of the separation membrane achieves equilibrium with the pressure of the oxygen dissolved solution. The circulation rate is preferably adjusted such that minimum water is lost from the oxygen carrier solution.

In the present invention, exposing the setting part of the carbon monoxide bonded oxygen carrier solution and the oxygen-dissolved solution to light means exposing the portion where the carbon monoxide bonded oxygen carrier encounters oxygen supplied at the periphery of the separation membrane to light. Examples of the light source include an incandescent light, halogen lamp, a light emitting diode, a sodium vapor lamp, or a metal halide lamp. The luminance of a single light source can be 500,000 Lm or more, but is preferably 1 to 500,000 Lm, and more preferably 100 to 200,000 Lm. In addition, two or more light sources each having the luminance mentioned above may be used in combination.

The carbon monoxide bonded oxygen carrier solution to be used in the present invention may contain a reducing agent. That is, a sample prepared by treating an oxygen carrier of the present invention by deoxygenation may include an antioxidant containing a reducing agent as an additive for suppressing an oxidation reaction of divalent heme iron present in the oxygen carrier into trivalent heme iron by oxygen and for preventing degradation of performance of the oxygen carrier.

Examples of the natural oxygen carriers treated by deoxygenation include hemoglobin originated from, for example, humans, bovine, or other living organisms; concentrated red blood cells or myoglobin originated from, for example, humans, bovines, or other living organisms; or hemocyanin originated from, for example, fish or other living organisms. Examples of the artificial oxygen carriers include highly-functional oxygen carriers that utilize natural oxygen carriers such as modified hemoglobin and hemoglobin-encapsulated liposomes; completely-synthesized oxygen carriers, such as compounds in which porphyrin metallic complexes inclusive of porphyrin derivatives are incorporated in albumin, albumin dimers, and albumin polymers, and perfluorocarbon; various kinds of modified hemoglobin; agents each including a heme complex in albumin, such as a porphyrin metal complex-including albumin, a porphyrin metal complex-including albumin dimer, a porphyrin metal complex-including albumin polymer, a PEG-modified porphyrin metal complex-including albumin, a PEG-modified porphyrin metal complex-including albumin dimer, and a PEG-modified porphyrin metal complex-including albumin polymer; and recombinant carriers such as recombinant hemoglobin, recombinant modified hemoglobin, modified recombinant hemoglobin, and recombinant hemoglobin-encapsulated liposomes, which can be obtained by gene recombination technologies. Among them, the hemoglobin-encapsulated liposomes, the PEG-modified phenylporphinato iron complex-including albumin or PEG-modified porphyrin metal complex-including albumin, and recombinant hemoglobin-encapsulated liposomes are preferable. In addition, as an additive, one or two or more of reducing agents selected from the group described below may be used.

Examples of the reducing agent include, for example, dithionous acid, dithionite (such as sodium dithionite), bisulfite (such as sodium bisulfite), sulfite (such as sodium sulfite and anhydrous sodium sulfite), pyrosulfite (such as sodium pyrosulfite), metabisulfite (such as sodium metabisulfite), Rongalite ($CH_2OHSO_2Na$), ascorbic acid or salts thereof (such as L-ascorbic acid and sodium L-ascorbate), erythorbic acid or salts thereof (such as sodium erythorbate), cysteine (cysteine hydrochloride is preferable), thioglycerol, α-thioglycerin, edetate (such as sodium edetate), citric acid, isopropyl citrate, dichlorisocyanurate (such as potassium dichlorisocyanurate), thioglycolate (such as sodium thioglycolate), thiomalate (such as sodium thiomalate), 1,3-butyleneglycol sodium pyrosulfite, butylhydroxyanisole (BHA), dibutylhydroxytoluene (BHT), propyl gallate, ascorbyl palmitate, dl-α-tocopherol, tocopherol acetate, natural vitamin E, d-δ-tocopherol, concentrated mixed tocopherol, a guaiac resin, nordihydro-guaiaretic acid (NDGA), L-ascorbyl stearate, soybean lecithin, ascorbyl palmitate, benzotriazole, pentaerythrityl-tetrakis[3-(3,5-di-t-butyl-4-hydroxyphenyl)propionate]2-mercaptobenzimidazole, calcium disodium ethylenediaminetetraacetate, and disodium ethylenediaminetetraacetate.

Of these, L-ascorbic acid or sodium L-ascorbate is preferable.

One kind of reducing agent selected from the group described above may be used alone, or two or more kinds of reducing agents may be used at the same time. The reducing agent need not be added depending on the conditions. In the case in which the reducing agent is added, the concentration of the reducing agent is preferably 0.01 g/L to 150 g/L, and more preferably 0.1 g/L to 10 g/L.

The oxygen carrier treated by deoxygenation may be combined with one or two or more kinds of agents selected from the group consisting of a reducing agent, electrolytes, saccharides, a pH adjuster, an isotonizing agent, and a polymer substance capable of imparting a colloid osmotic pressure, to thereby form a useful pharmaceutical composition.

A pharmaceutical composition including the oxygen carrier and one or two or more kinds of agents selected from the group composed of electrolytes, saccharides, a pH adjuster, an isotonizing agent, and a polymer substance capable of imparting a colloid osmotic pressure, refers to a pharmaceutical composition in a form allowing administration of an oxygen carrier into a living body and safe and effective development of its oxygen transport function. Examples of the form of the pharmaceutical composition include a transfusion preparation, a lyophilized preparation, a kit preparation, and a prefilled syringe.

Examples of the saccharides to be used for the pharmaceutical composition of the present invention include glucose, fructose, xylitol, maltose, sorbitol, sucrose, trehalose, mannitol, glycerin, lactose, erythritol, and dextrin.

Examples of the pH adjuster to be used for the pharmaceutical composition of the present invention include, adipic acid, ammonia water, hydrochloric acid, sodium caseinate, dried sodium carbonate, diluted hydrochloric acid, citric acid, sodium citrate, sodium dihydrogen citrate, glycine, glucono-δ-lactone, gluconic acid, sodium gluconate, crystal sodium dihydrogen phosphate, succinic acid, acetic acid, ammonium acetate, sodium acetate, diisopropanolamine, tartaric acid, D-tartaric acid, L-sodium tartrate, potassium hydroxide, calcium hydroxide, sodium hydroxide, magnesium hydroxide, sodium bicarbonate, sodium carbonate, triisopropanolamine, triethanolamine, and sodium salts of barbital.

Examples of the isotonizing adjusting agent to be used for the pharmaceutical composition of the present invention include aminoethyl sulfonic acid, sodium bisulfite, potassium chloride, calcium chloride, sodium chloride, benzalkonium chloride, magnesium chloride, fructose, xylitol, citric acid, sodium citrate, glycerin, crystal sodium dihydrogen phosphate, calcium bromide, sodium bromide, sodium hydroxide, and sodium tartrate dihydrate.

Examples of the polymer substance capable of imparting a colloid osmotic pressure to be used for the pharmaceutical composition of the present invention include dextran (low molecular weight dextran), hydroxyethyl starch (HES, average molecular weight 70,000), gelatin (modified gelatin), albumin (human live-plasma, human serum albumin, heated human plasma protein, human recombinant albumin), soda alginate, glucose, dextrose (D-glucose monohydrate), oligosaccharides (oligosaccharide), a decomposition product of polysaccharides, amino acid, and a decomposition product of protein.

The oxygen carrier to be used in the present invention is suspended in a phosphate buffer, a physiological saline solution, or the like. The suspension is adjusted to a pH of desirably 5.0 to 8.0, and more preferably 7.0 to 7.5. The suspension has a hemoglobin solution concentration of desirably 1 g/dL to 20 g/dL, and more preferably 5 g/L to 15 g/dL. The suspension has a lipid concentration of desirably 2.5 g/dL to 15 g/dL, and more preferably 4.0 g/dL to 7.5 g/dL.

Further, the porphyrin metal complex-including albumin or the PEG-porphyrin metal complex-including albumin has an rHSA concentration of desirably 0.5% to 25%, and more preferably 4.0% to 6.0%; and an iron content of desirably 0.3 mM to 15 mM, and more preferably 2.0 mM to 4.0 mM.

The pharmaceutical composition including the above-mentioned oxygen carrier containing the above-mentioned additives and the like desirably has physical properties including a colloid osmotic pressure of 1 mmHg to 50 mmHg; a crystalline osmotic pressure of 50 mOsm to 500 mOsm; and an oxygen affinity (oxygen partial pressure P50 providing a bonding ratio between the oxygen carrier and oxygen of 50%) of 5 Torr to 50 Torr.

The apparatus for removing carbon monoxide from an oxygen carrier which includes a separation membrane across which a carbon monoxide bonded oxygen carrier solution is set from an oxygen-dissolved solution; a light source for exposing the arrangement to light; and pumps for supplying respective solutions means a series of devices capable of removing carbon monoxide from the carbon monoxide bonded oxygen carrier. That is, the separation membrane may be in a planar form or a hollow fiber form, and the apparatus may be formed of any combination of devices as long as the carbon monoxide bonded oxygen carrier solution set across by the intermediation of the separation membrane from the oxygen-dissolved solution is exposed to light.

EXAMPLES

Hereinafter, the present invention will be described more specifically by using examples, but the present invention is not limited by the examples.

Preparation of Porphyrin Metal Complex-Including Albumin Inclusion Compound:

Carbon monoxide was bubbled through an ethanol solution of a 2-[8-(2-methyl-1-imidazolyl)octanoyloxymethyl]-5,10, 15,20-tetrakis[$\alpha,\alpha,\alpha,\alpha$,-o-(1-methylcyclohexanoylamino) phenyl]porphinato complex (available from Kanto Chemical Co., Inc.), to thereby prepare a 1.07 mM carbon monoxide bonded porphinato complex solution. 6.5 L of a 0.27 mM albumin solution dissolved in a 1/30 mM aqueous phosphate buffer solution (pH 7.4) was added to 1.6 L of the 1.07 mM porphinato complex solution, and the whole was mixed under stirring.

While 60 L of the 1/30 mM aqueous phosphate buffer solution (pH 7.4) was added to 8.1 L of the obtained mixed liquid, fixed ultrafiltration dialysis was performed by using an ultrafiltration device including a membrane with an ultrafiltration molecular weight of 30,000 (manufactured by Millipore Corporation), to thereby remove ethanol contained in the mixed liquid. Further, the mixed liquid was concentrated to 300 mL by using the same ultrafiltration device, to thereby obtain a desired dispersion of a porphyrin metal complex-including albumin compound (hereinafter, abbreviated as rHSA-FecycP dispersion) having an rHSA concentration of about 5% and an iron content of 3 mM.

Preparation of Hemoglobin-Encapsulated Liposome:

0.3 M of a pyridoxal 5'-phosphate (hereinafter, abbreviated as PLP) solution (24.8 mL) (solvent: aqueous NaOH solution), and 0.27 g of homocystein (hereinafter, abbreviated as Hcy) were added to a hemoglobin (hereinafter, abbreviated as Hb) solution ([Hb]=40 g/dL, 400 mL). The whole was adjusted to a pH of 7.4, stirred at 4° C. overnight, and filtered through a 0.22 μm filter (final concentration: Hb: 5.9 mmol/L, PLP: 17.3 mmol/L, Hcy: 5 mmol/L). The obtained liquid was subjected to degassing and carbon monoxide (hereinafter, referred to as CO) gas flow three times for carbon monoxylation (hereinafter, referred to as CO conversion) of Hb in the liquid, to thereby obtain a carbon monoxide bonded Hb solution.

Meanwhile, 20 g in total of a mixture of dipalmitoylphosphatidylcholine (hereinafter, abbreviated as DPPC)/cholesterol/1,5-dipalmitoyl-L-glutamate-N-succinic acid (10/10/2 in molar ratio) was dissolved in 1 L of benzene.

1 g of a composite (hereinafter, abbreviated as PEG-DSGE) prepared by bonding polyethylene glycol (hereinafter, abbreviated as PEG) to distearyl glutaryl ester was dissolved in 1 L of physiological saline. The obtained liquid was mixed into the mixture dissolved in benzene such that a PEG-DSGE concentration ratio was 0.3 mol % with respect to the total lipid amount, to thereby obtain a mixed liquid. Then, the mixed liquid was freeze dried, to thereby obtain uniformly dispersed lipid mixed powder.

20 g of the lipid mixed powder was added to the carbon monoxide bonded Hb solution ([Hb]=5.9 mmol/L, [PLP]= 17.3 mmol/L, [Hcy]=5 mmol/L, 400 mL) in small portions and was hydrated at 4° C. The resultant sample was stirred overnight by using a screw forced stirrer and then was adjusted into a particle size of 0.22 μm by using an extruder (manufactured by Lipex Biomembranes, Inc.), to thereby obtain a dispersion of a hemoglobin-encapsulated liposome (hereinafter, abbreviated as HbV) having a hemoglobin solution concentration of about 10 g/dL and a lipid concentration of 6 g/dL, 200 mL by ultra centrifuge.

Method of Evaluating Carbon Monoxide Ratio (Hereinafter, Abbreviated as CO-Hb Conversion Rate):

The artificial oxygen carrier recovered with time was diluted appropriately with a 1 mM phosphate buffer (pH 7.4), and 5 mL of the resultant was sealed in an ultraviolet cell (hereinafter, abbreviated as UV cell). Then, 10 mg to 30 mg of sodium dithionite with a purity of 75% or more was added thereto, and the whole was mixed. An absorption spectrum at a wavelength of 300 nm to 700 nm was measured, within 1 minute after the mixing, by UV-vis spectroscopy. The absorption spectrum included a maximum absorption derived from a carbon monoxide member at a wavelength of 427 nm; a maximum absorption derived from a deoxidized artificial oxygen carrier, that is, a deoxy-member (Deoxy member) at a wavelength of 443 nm; and an isosbestic point at a wavelength of 435 nm. The CO conversion rate was determined by the following equation.

$$CO\text{-}Hb \text{ conversion rate}(\%) = (Qs - Qo)/(Q100 - Qo) \times 100 \quad (\text{Eq. 1})$$

$$QS = ES427/ES435 \quad (\text{Eq. 2})$$

(Description of Symbols in the Equations)

Q100: Ratio of an absorbance of the sample having CO-Hb conversion rate of 100% at a wavelength of 427 nm to that at a wavelength of 435 nm.

Qs: Ratio of an absorbance of the measured sample at a wavelength of 427 nm to that at a wavelength of 435 nm Qo: Ratio of an absorbance of the sample having CO-Hb conversion rate of 0% at a wavelength of 427 nm to that at a wavelength of 435 nm ES427: Absorbance of the measured sample at a wavelength of 427 nm ES435: Absorbance of the measured sample at a wavelength of 435 nm Regarding the Number of Transmission:

This means the number of series of procedures counted as one round when all of the oxygen carrier passes from an oxygen carrier storage vessel (in FIG. 5, an oxygen carrier storage vessel 29) to a carbon monoxide bonded oxygen carrier recovery vessel (in FIG. 5, a carbon monoxide bonded oxygen carrier recovery vessel 36) through the hollow fiber membrane module (in FIG. 5, a hollow fiber membrane module sealed with urethane 31) and are then treated and recovered. In other words, the number of transmissions in the present procedures corresponds to the number of cycles, each in which an artificial oxygen carrier solution after completion of treatment is transferred from an artificial oxygen carrier storage vessel to a vessel for recovering the treated oxygen carrier and then returned to the hollow fiber membrane module.

Example 1

Carbon monoxide was removed from the rHSA-FecycP dispersion by using an apparatus schematically shown in FIG. 1. The apparatus shown in FIG. 1 includes an artificial oxygen carrier circulation vessel 1; an oxygen-dissolved solution circulation vessel 2; a hollow fiber membrane module 3; a light source 4; an artificial oxygen carrier circulation pump 5; an oxygen-dissolved solution circulation pump 6; an oxygen-dissolved solution supply pump 7; and an oxygen supply line 8.

In Example 1, a hollow fiber membrane module FB-50UGA (manufactured by NIPRO Corporation) was used as the hollow fiber membrane module 3 at room temperature. 200 mL of a 10 times diluted solution of the rHSA-FecycP dispersion was introduced into the artificial oxygen carrier circulation vessel 1, and the artificial oxygen carrier was circulated at a circulation rate of 200 mL/minute with the artificial oxygen carrier circulation pump 5.

Meanwhile, 2 L of the 1/30 mM aqueous phosphate buffer solution (pH 7.4) was introduced into the oxygen-dissolved solution circulation vessel 2, and the oxygen-dissolved solution was circulated at a circulation rate of 500 mL/minute with the oxygen-dissolved solution circulation pump 6. At this time, oxygen was supplied to the oxygen-dissolved solution circulation vessel 2 from the oxygen supply line 8 through bubbling at about 2 L/minute.

A 50 W halogen lamp was used as the light source 4, and the hollow fiber membrane module 3 was exposed to incandescent light of about 10,000 Lx from a distance of about 5 cm directly above.

The artificial oxygen carrier and the hollow fiber membrane module 3 were observed visually. Further, the artificial oxygen carrier was recovered from the artificial oxygen carrier circulation vessel 1 with time, and the CO-Hb conversion rate was used for understanding the system evaluation.

Figure 6:
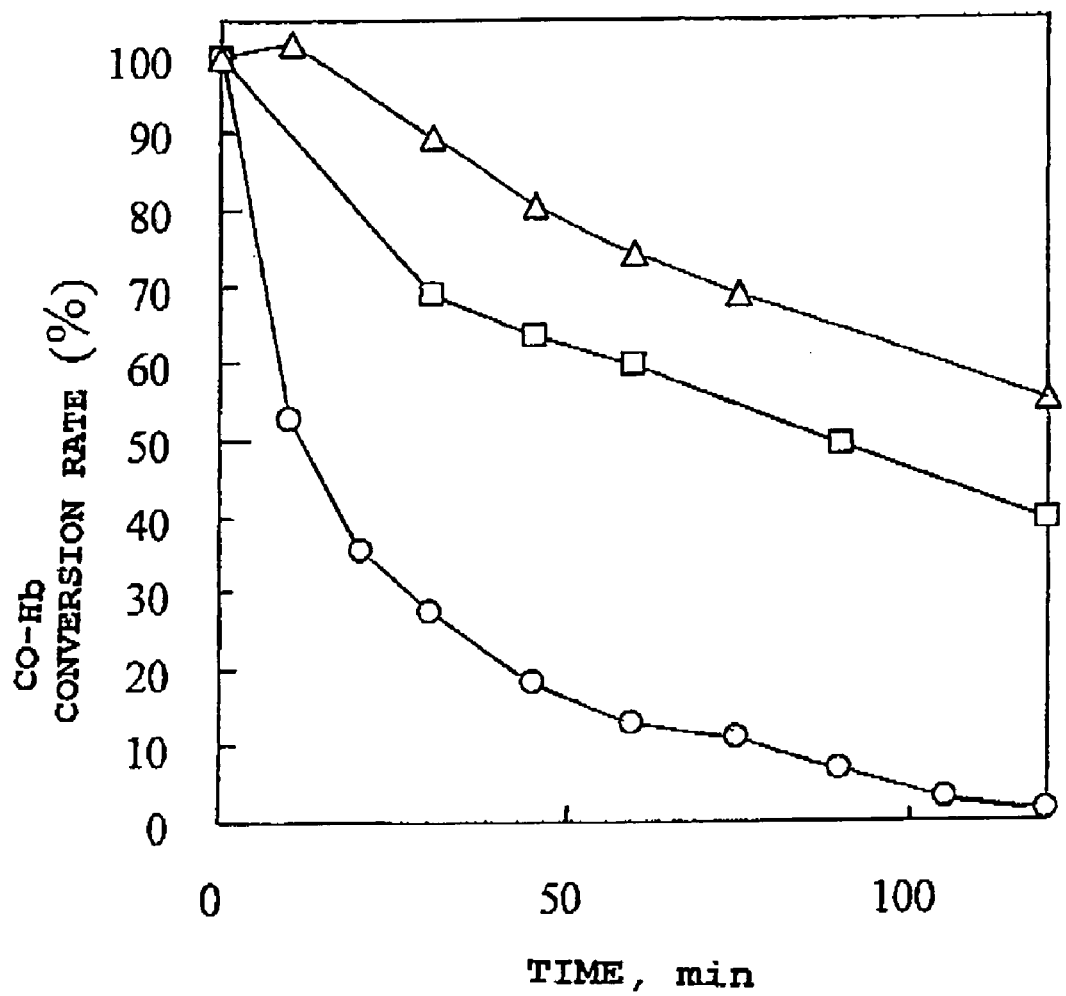
FIG. 6 is a graph showing change in carbon monoxide ratio (that is, CO-Hb conversion rate) with time in Examples 1 and 2 and Comparative Example 1. Symbol □ represents the CO-Hb conversion rate in Example 1, and symbol ○ represents the CO-Hb conversion rate in Example 2. Symbol ∆ represents the CO-Hb conversion rate in Comparative Example 1.

As a result, FIG. 6 shows that the CO-Hb conversion rate (□ in FIG. 6) reduced to 69% in 30 minutes, 60% in 60 minutes, and 39% in 120 minutes, and carbon monoxide was removed rapidly from the artificial oxygen carrier. No denaturation of proteins and the like by concentration of the artificial oxygen carrier, no degradation in membrane performance by drying of the separation membrane, no degradation of the separation membrane by heat, or no denaturation of the artificial oxygen carrier was observed in the artificial oxygen carrier circulation vessel 1 or the hollow fiber membrane module 3.

Example 2

Carbon monoxide was removed from the rHSA-FecycP dispersion by using the same apparatus and sample as those in Example 1 and in the same manner as in Example 1 except that a 500 W halogen lamp was used as the light source 4 and incandescent light of about 20,000 Lx or more was supplied.

As a result, FIG. 6 shows that the CO-Hb conversion rate (○ in FIG. 6) reduced to 27% in 30 minutes, 13% in 60 minutes, and 1.5% in 120 minutes, and carbon monoxide was removed rapidly from the artificial oxygen carrier. No denaturation of proteins and the like by concentration of the artificial oxygen carrier, no degradation in membrane performance by drying of the separation membrane, no degradation of the separation membrane by heat, or no denaturation of the artificial oxygen carrier was observed in the artificial oxygen carrier circulation vessel 1 or the hollow fiber membrane module 3.

Comparative Example 1

Figure 2:
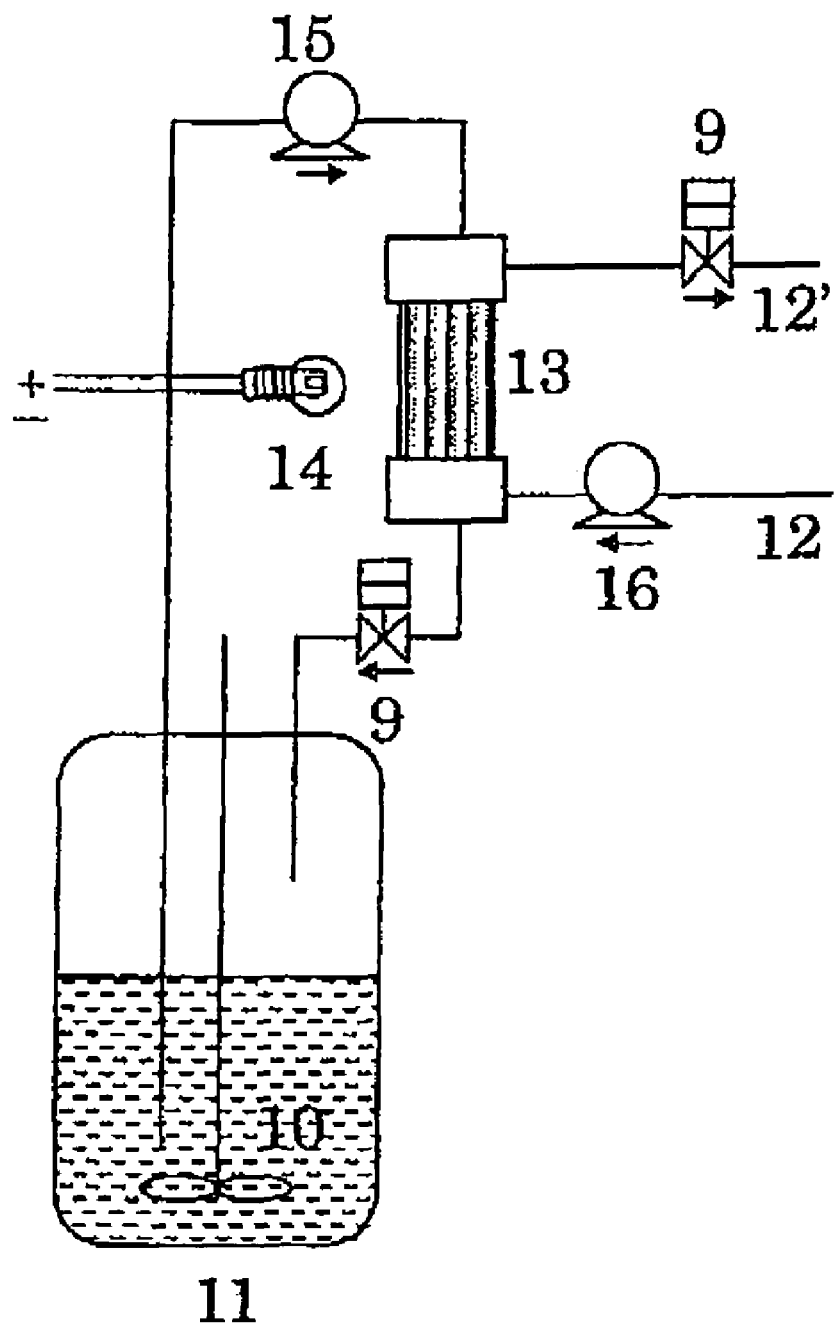
FIG. 2 shows a diagram explaining a conventional apparatus for removing carbon monoxide with a hollow fiber membrane by using an oxygen gas.

Carbon monoxide was removed from the rHSA-FecycP dispersion by using an apparatus shown in FIG. 2 through a conventional method in which an oxygen gas is supplied. That is, Comparative Example 1 differs from Example 1 in that oxygen gas is supplied instead of the oxygen-dissolved solution.

The apparatus shown in FIG. 2 includes: an artificial oxygen carrier circulation vessel 11; an oxygen gas supply line 12; a hollow fiber membrane module 13; a light source 14; an artificial oxygen carrier circulation pump 15; and an oxygen gas supply pump 16.

Carbon monoxide is removed from the artificial oxygen carrier supplied from the artificial oxygen carrier circulation vessel 11 in the hollow fiber membrane module 13 by an oxygen gas supply line 12 and light from the light source 14, and the oxygen carrier is returned to the artificial oxygen carrier circulation vessel 11.

The oxygen gas is supplied directly into the hollow fiber membrane module 13 from the oxygen gas supply line 12 with the oxygen gas supply pump 16, and carbon monoxide is discharged while the oxygen gas is replenished.

In Comparative Example 1, a hollow fiber membrane module FB-50UGA (manufactured by NIPRO Corporation) was used as the hollow fiber membrane module 13 in the same manner as in Example 1. 200 mL of a 10 times diluted solution of the rHSA-FecycP dispersion was introduced into the artificial oxygen carrier circulation vessel 11, and the artificial oxygen carrier was circulated at a circulation rate of 200 mL/minute with the artificial oxygen carrier circulation pump 15. Meanwhile, an oxygen gas was directly blown into the hollow fiber membrane module 13 at 2,000 mL/minute with the oxygen gas supply pump 16. A 50 W halogen lamp was used as the light source 14, and the hollow fiber membrane module 13 was exposed to incandescent light of about 10,000 Lx from a distance of about 5 cm directly above.

As a result, FIG. 6 shows that the CO-Hb conversion rate (Δ in FIG. 6) reduced to 89% in 30 minutes, 74% in 60 minutes, and 55% in 120 minutes. Further, denaturation of proteins and the like by concentration of the artificial oxygen carrier, degradation in membrane performance by drying of the separation membrane, degradation of the separation membrane by heat, and denaturation of the artificial oxygen carrier were observed in the artificial oxygen carrier circulation vessel 11 or the hollow fiber membrane module 13.

Comparative Example 2

The rHSA-FecycP dispersion was subjected to carbon monoxide removal by using the same apparatus and sample as those of Comparative Example 1 and in the same manner as in Comparative Example 1 except that a 500 W halogen lamp was used as the light source 4 and the hollow fiber membrane module 13 was exposed to incandescent light of about 20,000 or more.

As a result, the artificial oxygen carrier solution in the hollow fiber membrane module 13 and the artificial oxygen carrier circulation vessel 11 showed abnormal temperature increase to 65° C. or higher in 20 minutes. An outer covering of the hollow fiber membrane module 13 melted by heat of the 500 W halogen lamp, and the hollow fiber membrane was clogged. Denaturation of the artificial oxygen carrier solution was observed.

Test Example

Figure 8:
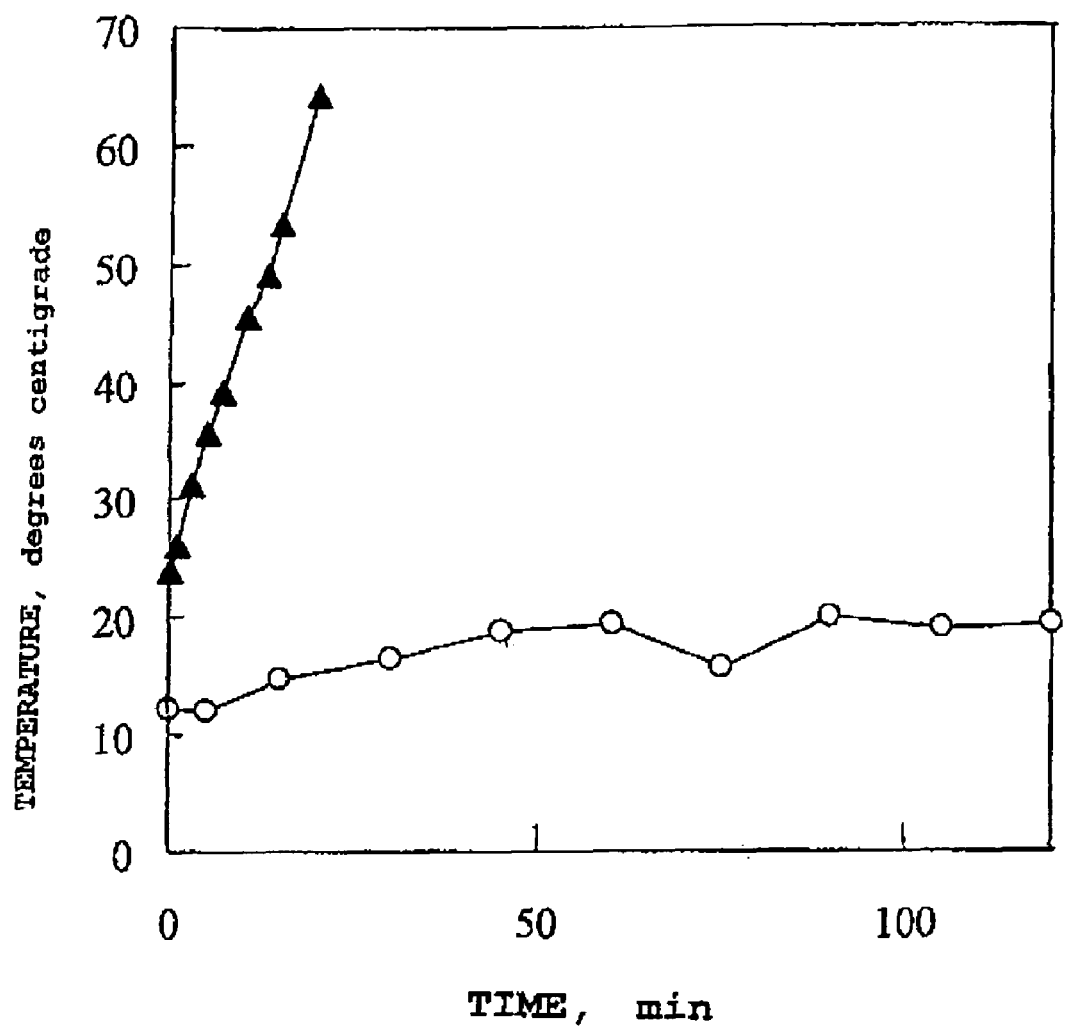
FIG. 8 is a graph showing change in temperature of an artificial oxygen carrier solution in an oxygen carrier circulation vessel with time in Example 2 and Comparative Example 2. Symbol ○ represents the results of measurement with time in Example 2. Symbol ▲ represents the results of measurement with time in Comparative Example 2.

The temperature of the artificial oxygen carrier solution in the artificial oxygen carrier circulation vessel and its change with time in Example 2 and Comparative Example 2 were studied. As a result, as shown in FIG. 8, no increase in temperature of the artificial oxygen carrier solution was observed through use of the method of present invention as in Example 2 (○ in FIG. 8). However, the temperature of the artificial oxygen carrier solution far exceeded 60° C. in about 20 minutes through use of a method in which an oxygen gas is supplied as in Comparative Example 2 (▲ in FIG. 8). The temperature far exceeding 60° C. causes denaturation of proteins, and thus the method in which an oxygen-dissolved solution is supplied and the apparatus of the present invention are excellent in view of not causing a temperature increase.

Example 3

The hemoglobin-encapsulated liposome dispersion was subjected to carbon monoxide removal by using the same apparatus and sample as those of Example 1 and in the same manner as in Example 1 except that the hemoglobin-encapsulated liposome dispersion was used instead of the rHSA-FecycP dispersion.

Figure 7:
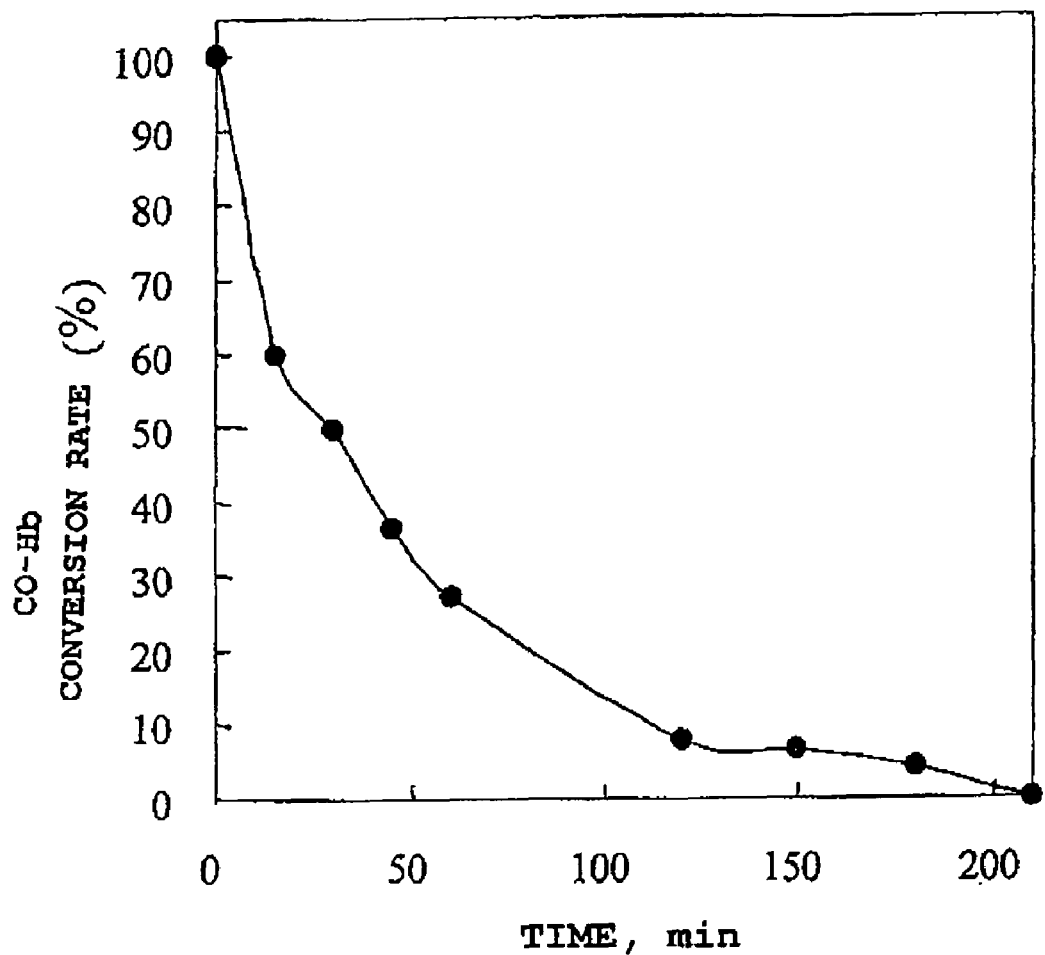
FIG. 7 is a graph showing change in carbon monoxide ratio (that is, CO-Hb conversion rate) with time in Example 3.

As a result, FIG. 7 shows that the CO-Hb conversion rate reduced to 50% in 30 minutes, 27% in 60 minutes, 8% in 120 minutes, and about 0% in 210 minutes, and carbon monoxide was removed rapidly from the artificial oxygen carrier. No denaturation of proteins and the like by concentration of the artificial oxygen carrier, no degradation in membrane performance by drying of the separation membrane, no degradation of the separation membrane by heat, or no denaturation of the artificial oxygen carrier was observed in the artificial oxygen carrier circulation vessel 1 or the hollow fiber membrane module 3.

Example 4

The rHSA-FecycP dispersion was subjected to carbon monoxide removal by using the same apparatus and sample as those of Example 1 and in the same manner as in Example 1, that is, the apparatus shown in FIG. 4 except that the artificial oxygen carrier was not circulated to the artificial oxygen carrier circulation vessel 1; three hollow fiber membrane modules were connected in series; and the sample allowed to pass through the hollow fiber membrane modules was recovered continuously.

That is, the apparatus of FIG. 4 includes an artificial oxygen carrier storage vessel 17; an oxygen-dissolved solution circulation vessel 18; a hollow fiber membrane module A 19; a hollow fiber membrane module B 20; a hollow fiber membrane module C 21; a light source A 22; a light source B 23; a light source C 24; an artificial oxygen carrier circulation pump 25; an oxygen-dissolved solution circulation pump 26; an oxygen supply line 27; and a vessel 28 for recovering an artificial oxygen carrier subjected to carbon monoxide removal.

As a result, the artificial oxygen carrier subjected to carbon monoxide removal can be collected continuously at 200 mL/minute. The artificial oxygen carrier had a CO-Hb conversion rate of 89% after passing through the hollow fiber membrane module A, 77% after passing through the hollow fiber membrane module B, and 67% after passing through the hollow fiber membrane module C. The results suggest that a pharmaceutical composition having a CO-Hb conversion rate of about 0% can be obtained continuously by increasing the number of hollow fiber membrane modules.

Further, no denaturation of proteins and the like by concentration of the artificial oxygen carrier, no degradation in membrane performance by drying of the separation membrane, no degradation of the separation membrane by heat, or no denaturation of the artificial oxygen carrier was observed in the artificial oxygen carrier circulation vessel 11 or the hollow fiber membrane module 13.

Example 5

A module was prepared by applying an isocyanate-based resin in a circular pattern on the central portion of the cross section of the bundle of hollow fibers at an inlet of an inner port of the hollow fiber module so as to allow a treatment solution to run only along the outer periphery of the bundle of hollow fibers in the module, which can be easily exposed to light.

In other words, the bundle of hollow fibers in the port of the hollow fiber membrane module FB-210UGA (manufactured by NIPRO Corporation) has a cross-sectional diameter of 3.6 to 3.8 cm. Thus, the isocyanate-based resin was applied on the cross-section of the bundle of hollow fibers so as to be applied concentrically in a circular pattern of 3.0 to 3.2 cm in diameter. Consequently, the bundle of hollow fibers in a module, which allows the treatment solution to pass through a cylindrical portion with a thickness of about 2 to 4 mm, was obtained.

Figure 5:
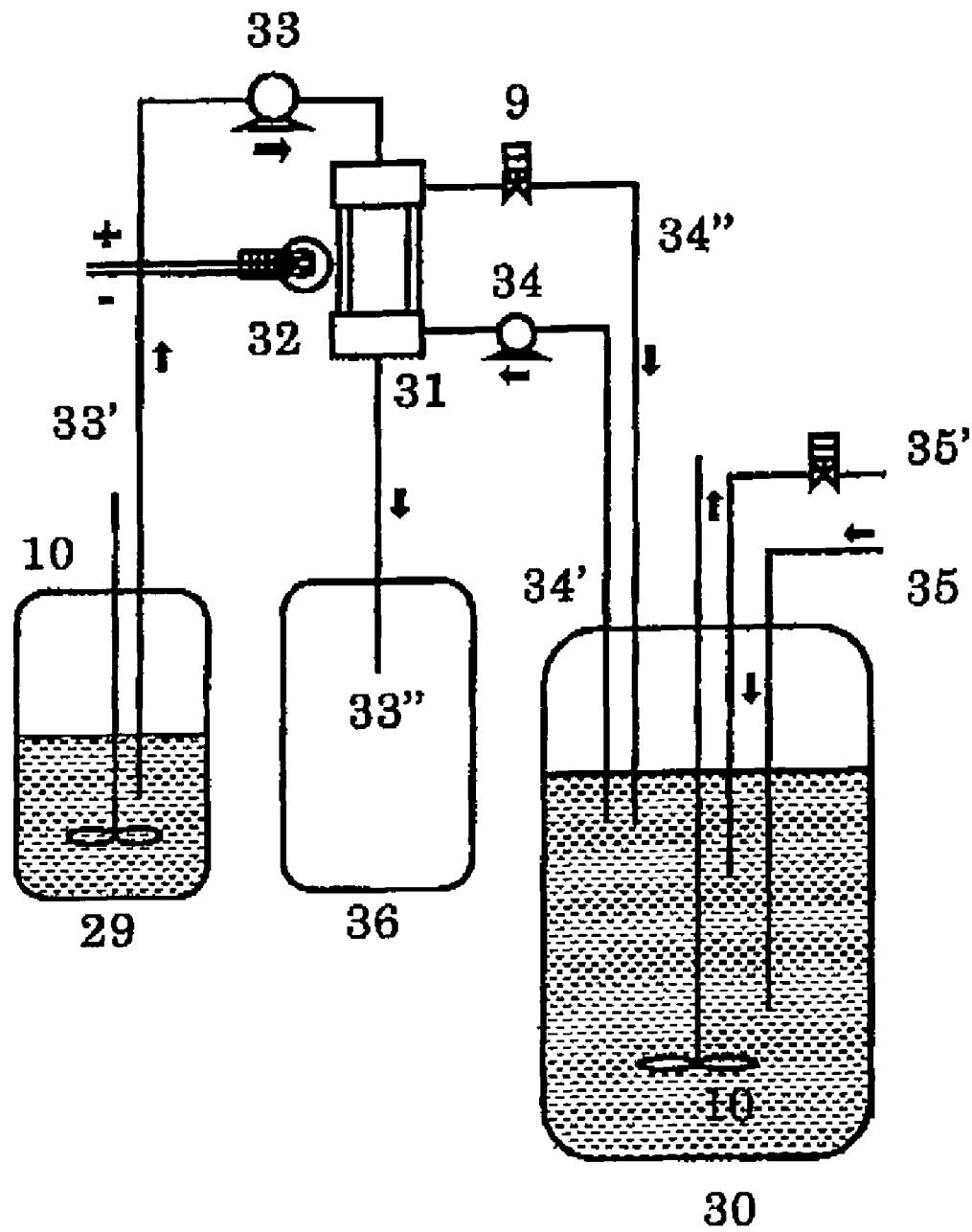
FIG. 5 shows a diagram explaining an apparatus for continuously removing carbon monoxide according to the present invention with a urethane-sealed hollow fiber membrane module by using an oxygen-dissolved solution. The hollow fiber membrane module 31 is represented in cross section, and the vertical lines thereof represent that hollow fibers are vertically arranged and the flow path in the central part of the hollow fiber membrane module is thus plugged and unable to work.
Figure 9:
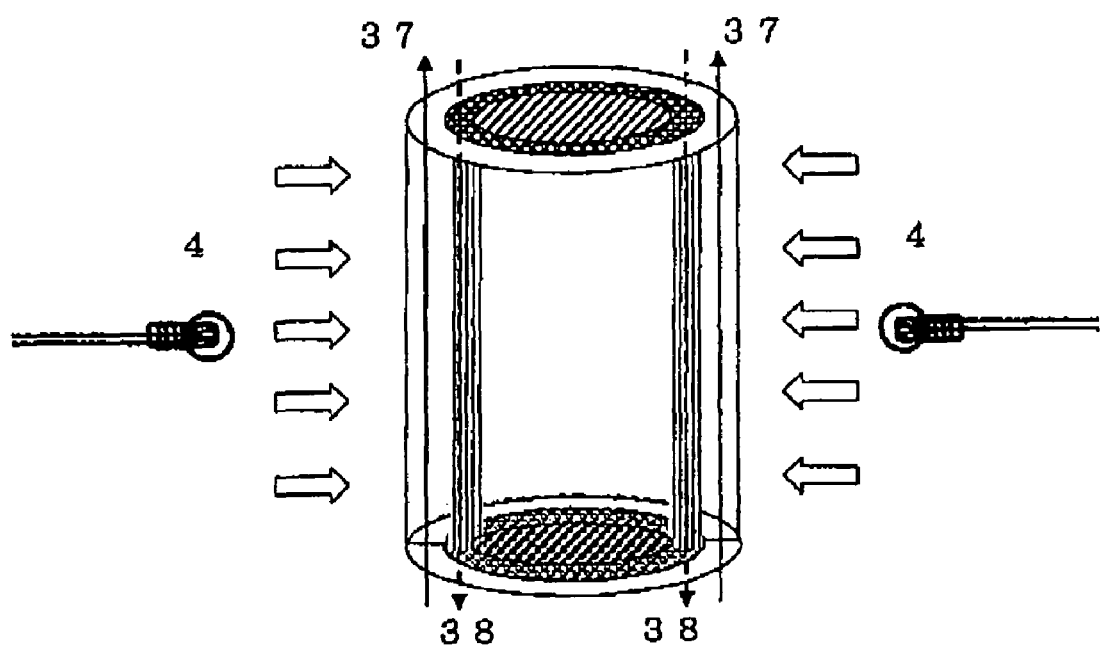
FIG. 9 shows a diagram explaining a highly-effective module according to the present invention using an urethane-sealed hollow fiber membrane module. Both the oxygen carrier solution and the oxygen-dissolved solution flow in opposite directions with respect to each other through a hollow fiber membrane. They are expressed by the arrow of a broken line and the arrow of a solid line, respectively. The hollow fiber membrane is represented as one present in a bundle form as a flow path of an oxygen carrier at the second cylindrical position from the outside, being illustrated in a polka-dot pattern. However, it is only expressed in vertical lines on both sides of the cylinder, and the front or back surface or the like are abbreviated. A bundle of hollow fiber membranes is present at the central position of the cylinder represented by a shaded area. However, the upper and bottom thereof were sealed with urethane and each of them is a portion which does not function as a flow path of an oxygen carrier.
Figure 10:
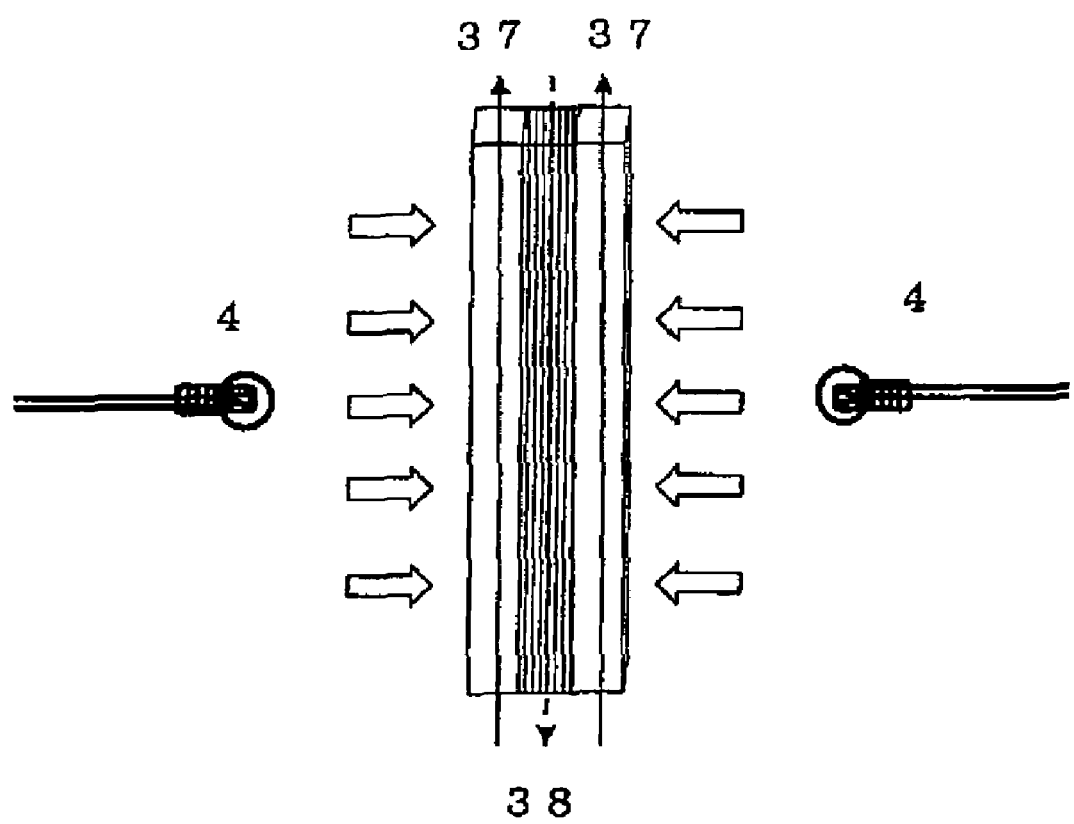
FIG. 10 shows a diagram explaining a highly-effective module according to the present invention using an urethane-sealed hollow fiber membrane module. Both the artificial oxygen carrier solution and the oxygen-dissolved solution flow in opposite directions with respect to each other through a hollow fiber membrane. They are illustrated by the arrow of a broken line and the arrow of a solid line, respectively. The hollow fiber membrane is represented as a single hollow fiber membrane or as hollow fiber membranes present in a bundle. It is expressed in vertical lines.

Removal of carbon monoxide from a hemoglobin-encapsulated liposome was carried out by the same device, sample, and method as those of Example 1, except that a system for continuously collecting the dispersion of sample hemoglobin-encapsulated liposome transmitted through a module of an urethane-sealed hollow membrane module by being connected to the urethane-sealed hollow fiber membrane module without circulating the artificial oxygen carrier to the oxygen carrier circulation vessel 1 was used. Such a system of devices is shown in FIG. 5. As is different from the hollow fiber membrane module in the prior description, the module used was a single urethane-sealed hollow fiber membrane module 29 as shown in FIG. 9 or 10.

Figure 11:
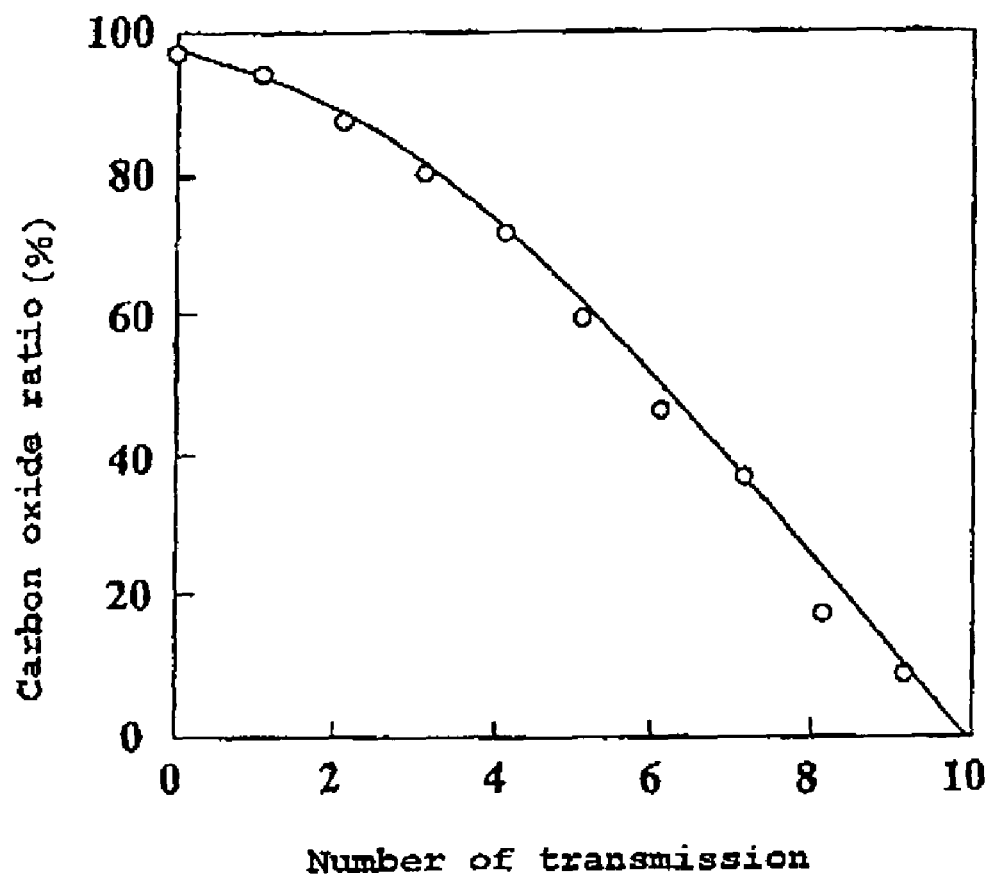
FIG. 11 is a graph showing the relationship between the number of transmission and the carbon oxide ratio (that is, CO conversion rate) in Example 5.

As a result, the rate of removal of carbon monoxide was decreased to, as shown in FIG. 11, 91% by one cycle of transmission, 78% by three cycles of transmission, and 3% by ten cycles of transmission, so that removing carbon monoxide from the artificial oxygen carrier could be quickly performed. Furthermore, in the oxygen carrier circulation vessel 1 and the hollow fiber membrane module 3, no denaturation of a protein or the like due to a condensation of the artificial oxygen carrier, no decrease in membrane performance due to drying of the separation membrane, no deterioration of the separation membrane due to heat, and no alternation of the artificial oxygen carrier were observed.

On the other hand, a system in which a commercially available module was directly installed in the system as shown in FIG. 5 had a low efficiency of 96% by one cycle of transmission and 84% by three cycles of transmission, compared to the present module.

INDUSTRIAL APPLICABILITY

The oxygen carrier obtained in the present invention can be used in medical fields for oxygen supply to an ischemic site or tumor tissue, for blood transfusion to a patient with massive bleeding, for an organ preservation perfusion fluid, for an extracorporeal circulation fluid, for a cell culture medium, and the like.

This application claims priority of Japanese Patent Application Nos. 2005-119057 filed Apr. 15, 2005, and 2006-38716 filed Feb. 16, 2006, which are incorporated herein by reference.

The invention claimed is:

1. A method of removing carbon monoxide from a carbon monoxide bonded oxygen carrier comprising:
setting a solution of a carbon monoxide bonded oxygen carrier across a separation membrane from an oxygen-dissolved solution; and exposing the separation membrane as a reaction plane to light.

2. The method of removing carbon monoxide from a carbon monoxide bonded oxygen carrier according to claim 1, wherein the separation membrane comprises a hollow fiber separation membrane.

3. The method of removing carbon monoxide from a carbon monoxide bonded oxygen carrier according to claim 1, wherein the oxygen carrier of the carbon monoxide bonded oxygen carrier is one material or a combination of two or more kinds selected from the group consisting of a hemoglobin-encapsulated liposome; a porphyrin metal complex-including albumin; a porphyrin metal complex/PEGylated albumin composite; a hemoglobin solution; a cross linked hemoglobin; a polymerized hemoglobin; and a PEGylated hemoglobin.

4. An apparatus for removing carbon monoxide from a carbon monoxide bonded oxygen carrier comprising:
a separation membrane having first and second opposing sides for separating a carbon monoxide bonded oxygen carrier solution from an oxygen-dissolved solution;
a light source for exposing the separation membrane as a reaction plane to the light;
a first pump for supplying the carbon monoxide bonded oxygen carrier solution to the first opposing side of the separation membrane; and
a second pump for supplying the oxygen-dissolved solution to the second opposing side of the separation membrane.

5. The apparatus for removing carbon monoxide from a carbon monoxide bonded oxygen canter according to claim 4, wherein the separation membrane comprises a hollow fiber separation membrane.

6. The apparatus for removing carbon monoxide from a carbon monoxide bonded oxygen carrier according to claim 4, wherein said first and second pumps are arranged such that the carbon monoxide bonded oxygen carrier solution and the oxygen-dissolved solution are caused to flow in opposite directions on the first and second opposing sides of the separation membranes.

* * * * *